US00RE38672E

(19) United States
(12) Reissued Patent
Grinblat

(10) Patent Number: US RE38,672 E
(45) Date of Reissued Patent: Dec. 21, 2004

(54) SLIT LAMP WITH AUXILIARY LAMP PRODUCING LINE OF LIGHT, ASPHERIC LENS HOLDER AND INVERTER

(76) Inventor: Avi Grinblat, 25 Central Park West, Apt. 4V, New York, NY (US) 10023

(21) Appl. No.: 10/125,366

(22) Filed: Apr. 16, 2002

Related U.S. Patent Documents

Reissue of:
(64) Patent No.: 6,050,688
Issued: Apr. 18, 2000
Appl. No.: 09/173,193
Filed: Oct. 15, 1998

(51) Int. Cl.[7] ..... A61B 3/10
(52) U.S. Cl. ..... 351/214
(58) Field of Search ..... 351/205, 206, 351/214, 221, 245, 246; 353/28, 29; 359/388, 649; 600/249

(56) References Cited

U.S. PATENT DOCUMENTS 3,285,242 A * 11/1966 Wallace ..... 600/249
3,790,249 A * 2/1974 Treace ..... 359/388
4,978,216 A * 12/1990 Liljegren et al. ..... 353/28
5,774,271 A * 6/1998 Lagerway et al. ..... 359/649

* cited by examiner

*Primary Examiner*—George Manuel
(74) *Attorney, Agent, or Firm*—Fay Kaplun & Marcin, LLP

(57) ABSTRACT

An auxiliary lamp for a slit lamp device used in eye examination, to improve digital photography of the eye being examined, includes a casing and a fiber optic bundle terminating in a glued and polished end face, which end face forms a light emitting line. A cylindrical lens is positioned in front of the end face and is adjusted by a finger-operated screw device to be moved toward, and away from, the end face to focus the line of light.

54 Claims, 6 Drawing Sheets

SLIT LAMP WITH AUXILIARY LAMP PRODUCING LINE OF LIGHT, ASPHERIC LENS HOLDER AND INVERTER

Matter enclosed in heavy brackets [ ] appears in the original patent but forms no part of this reissue specification; matter printed in italics indicates the additions made by reissue.

FIELD OF THE INVENTION

The present invention relates to medical devices and more particularly to an illuminating lamp for producing either a focused line of light or diffused light and used especially by ophthalmologists as an auxiliary lamp on a slit lamp in eye examinations and photographic documentation.

BACKGROUND OF THE INVENTION

A widely used instrument used by ophthalmologists for eye examinations is called a "slit lamp" biomicroscope (slit lamp diagnostic microscope). The instrument consists, generally, of fixed-frame posts supporting a headrest to receive the chin and forehead of a patient, and a movable base. A stereomicroscope is mounted on the base and the base is moved, in the X-Y-Z directions, by the user. A lamp is mounted to shine on the eye being examined and a control device, in front of the lamp, produces a slit of light, e.g., an elongated line of light of about 100,000 to 600,000 Lux.

That slit of light is focused on the patient's eye. Some slit lamps permit the length of the beam to be changed, i.e., 0.2 to 8 mm or more, and to be rotated about the patient's head and to be angled, i.e., rotated 20 degrees from vertical. The ophthalmologist looks at the eye being examined, generally through a stereo microscope mounted on the stand and also through a lens which is generally held by hand.

This type of slit lamp is available from Haag-Streit AG, i.e., Model 900 BQ; Rodenstock, i.e., Model RO 5000; Reichert, i.e., Model Xcel; D. F. Vasconcellos; Nikon; and others.

Although this type of slit lamp has proven satisfactory for eye examinations, it is not adapted for precision electronic/digital photography of the eye. For example, in "telemedicine" a patient at a local facility (for example, a small-town ophthalmologist office) is being examined. A photograph (video or still picture) of his eye is transmitted, in real time, to a center (for example, a university hospital) to obtain a consultation by a cornea specialist. A picture of the eye is taken using a high-resolution color digital camera, transmitted over a broadband telecommunication channel and displayed on a high-resolution monitor. However, the picture may not be satisfactory to provide an accurate remote diagnosis because the slit lamp's illumination of the patient's eye is not illuminated satisfactorily for accurate photography. The ophthalmologist, using his eyes and skill, can see more than shows in a high resolution digital photograph.

U.S. Pat. No. 5,196,874 is entitled "Slit Lamp Apparatus With Peripheral Illumination." It, and the present invention, provide an auxiliary lamp (additional illuminating device) to shine on the eye undergoing examination in addition to the slit illuminating device. The '874 patent's auxiliary lamp is a tube which is rotatably mounted on the slit lamp frame.

Other patents that relate to slit lamps include U.S. Pat. Nos. 4,868;383; 3,403,957; 5,099,354; 3,652,153; and 5,018,851; the above-listed patents being incorporated by reference.

SUMMARY OF THE INVENTION

In accordance with the present invention an auxiliary lamp is provided. A finger-operated knob moves a cylindrical lens to provide either a focused line of light or diffused light. One or two of these auxiliary lamps are used, in addition to the conventional slit lamp, to provide side illumination on an eyeball undergoing examination, especially for accurate digital photography of the eye.

The light is generated by a bulb within a lamp housing. The bulb and housing are used to generate light to a fiber optic bundle. An adjustable filter disc is positioned between the bulb and the fiber optic bundle to vary the amount of light reaching the fiber optic bundle. In addition, heat (IR) and UV filters are provided to remove heat and UV (Ultra-Violet) from the light beam before it reaches the optic fiber bundles. The disc has a series of zones and each zone has holes of a uniform size. The size of the holes differs as between zones. As the disk is rotated either more, or less, light passes through the disk. The disk controls the amount of light transmitted from the bulb to the fiber optic bundle without altering the light's color temperature.

A fiber optic connector is positioned on the lamp housing and has two inputs to receive two fiber optic bundles (left and right bundles). Each fiber optic bundle leads to an auxiliary slit lamp. The fiber optic bundles are random bundles of fine glass optic fibers, for example, 1,000–10,000 fibers in each bundle, and each bundle is protected by a flexible sheath.

Each auxiliary lamp is at a free end of an optic fiber bundle. The auxiliary lamp consists of an elongated and flat housing whose height is about the height of the normal eye socket, i.e., 1.5 to 2.5 cm. The ends of the fibers are randomly arranged and firmly held in the housing, arranged and glued to form an elongated rectangular end face line viewed from the end, i.e., 2 cm long and 0.2 to 0.5 mm wide. A cylindrical lens is positioned in front of the end face of the fiber optic bundle (line) to focus the light. Preferably the lens is elongated, i.e., 2 cm in height, and round in cross-section. A finger-operated knob and screw mechanism, on the housing, mounts the lens and allows its movement toward, or away, from the fiber bundle end face to focus or to diffuse the light. The light may be micrometrically focused to form a line of light, or may be unfocused to form a diffused illumination. The line of light provides a preset focus to enable viewing and photography in sharp focus of the eyelids, cornea, iris and the anterior part of the natural lens.

The auxiliary lamp housing is preferably mounted on a fixed post of the slit lamp frame using a precision double ball joint mounting device. The user may adjust the distance from the auxiliary lamp to the eye and may adjust its angle relative to the normally vertical slit lamp's illumination.

The eye being examined is imaged using a high resolution digital still or motion camera which generates a video-compatible signal, such as the Sony DKC 5000 (Cat's eye camera). It can produce still pictures or moving images in video resolution and digital high resolution, more than 1500×1100 pixels. Two cameras mounted on either side can show stereo.

The auxiliary lamp can be used, depending on its focus as a background illuminator or to illuminate the entire cornea. Its adjustability, by movement of the cylindrical lens, permits changes in focus and also permits the width of the beam to be varied.

The auxiliary lamp produces a totally cold light which gives a constant color temperature, permitting accurate digital imaging. The use of two auxiliary lamps, with left and right fiber optic bundles, permits lighting of the same eye from two directions and, using a special device, simultaneous examination and comparison of a patient's left and right eyes. The regular slit lamp may be turned off and the auxiliary lamp may be used to focus light on the retina.

The auxiliary lamp of the present invention is also adapted for use in eye surgery, especially corneal refractive surgery (without a slit lamp) and for close examination and surgery on the skin. In refractive surgery the lamp does not produce an objectionable reflection from the eye's cornea.

The present invention also provides for mounting a lens, preferably an aspheric lens, on a double four-joint mount. That mount permits the aspheric lens to be accurately positioned near the eye being examined without being hand-held. The aspheric lens is mounted at a fixed distance from the microscope. The ophthalmologist's hand is now free as it is not carrying an examination lens. The bottom of the lens mount is fixed to the movable portion of the slit lamp stand so that it moves along with the stereo microscope. This permits the digital picture, which may be a still photograph or a moving video, to be taken through the microscope and the aspheric examination lens without shaking due to hand motion.

The auxiliary lamp may be used to shine a line of light through the double convex aspheric lens in order to illuminate the retina. Its lens may be adjusted to provide either a diffused or focused light on the retina. In this use it becomes a miniature portable slit lamp.

Preferably the stereo microscope is fitted or retrofitted with an inverter. The inverter changes the image's orientation (left to right and right to left) and the vertical direction (up to down) and provides a normal image of the eye right side up. The aspheric lens inverts the normal image and the inverter reinverts that image so the ophthalmologist sees a normal upright image. The microscope inverter's normal image (correct side up) permits the ophthalmologist to observe the retina correct side up, to move his hand, and hand-held instruments, in a normal manner—and not in reverse as would be required without the inverter. He may view the eye being examined through the aspheric lens to catch the center of the eye in the center of the microscope field of view and flip the inverter into the optical path to obtain the desired reinverted image.

DETAILED DESCRIPTION OF THE INVENTION

Figure 1:
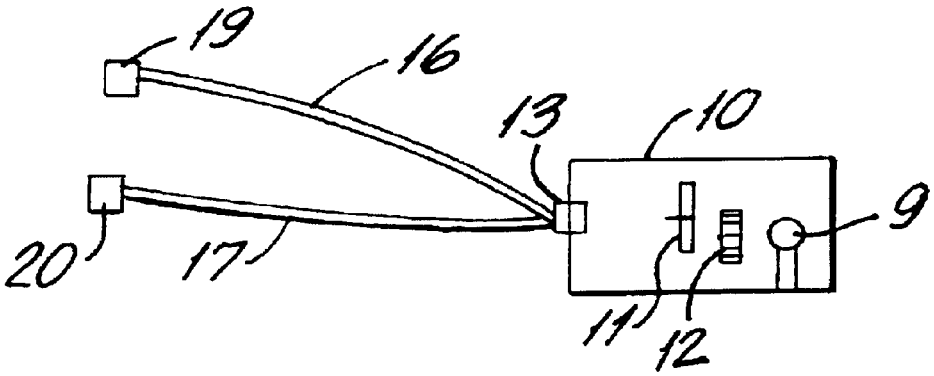
FIG. 1 is a cross-sectional diagram of the auxiliary lamp system of the present invention.
Figure 4A:
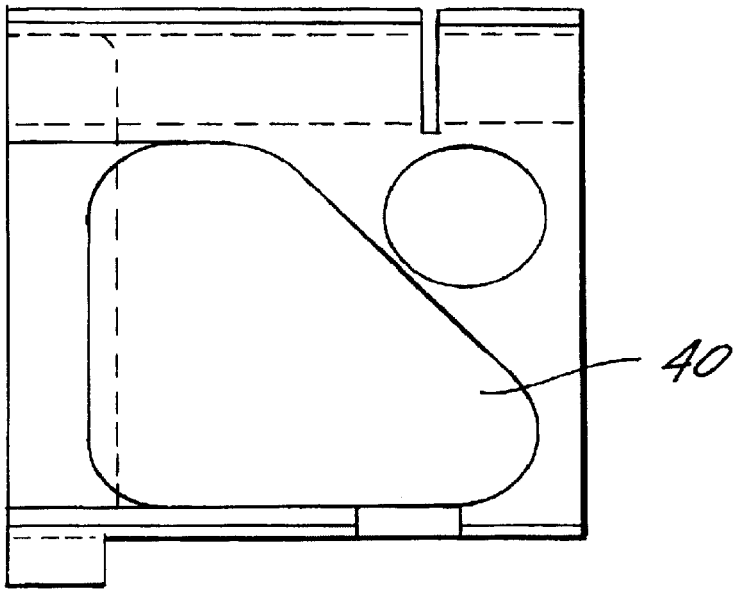
FIG. 4A is a side view of the interior of a lamp portion of the lamp device.
Figure 4B:
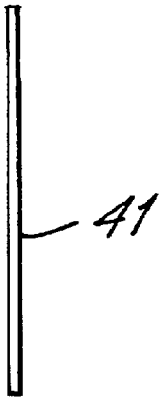
FIG. 4B is a front view of the end of the fiber optic bundle.
Figure 4C:
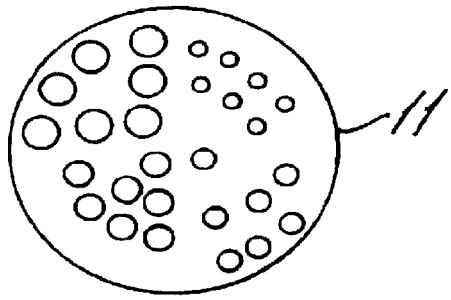
FIG. 4C is a front plan view of the adjustment disk used in the bulb housing.

As shown in FIG. 1 a fiber optic illuminator comprises a bulb housing 10 and a high intensity focused quartz halogen bulb 9, for example, a quartz halogen bulb of 150 W and may include a cooling fan. The light from the bulb passes through a manual iris comprising an adjustment disk 11 (see FIG. 4C) which is finger-rotated using a knob 12 rotatably mounted on housing 10 and connected through gears to the disk 11. The light passes through disk 11 and into a double fiber optic bundle connector 13 (light guide adapter), also mounted on the housing 10. The connector 13 has two plug inserts 14,15, each of which receives a fiber optic bundle 16,17, respectively. The disk 11 has four sectors (zones) with differently sized holes to control the amount of light. The disk 11 is rotated until one of its sectors, or parts of two sectors, are between the bulb and connector 13.

Each fiber optic bundle (fiber optic light guide) consists of a randomly arranged bundle of thin glass optical grade optic fibers, for example, 1,000–10,000 glass fibers in each bundle, or thin plastic polymer fibers, i.e., 0.5 mm with one row of fibers (40 fibers). Each fiber operates by a total internal reflection and consists of a thin 10 micron–250 micron glass fiber having an inner core of one index of refraction and an outer clad of a lower index of refraction. The fibers are covered by a protective flexible plastic sheath, for example, of PVC (polyvinylchloride), polyethylene or a coiled metal jacket.

Each fiber bundle 16,17 terminates in a lamp 19,20 (auxiliary lamp). Alternatively, and not shown, a liquid light guide or glass or plastic fiber optic light guide may be used to transmit light from the bulb housing to a connector on the lamp 19,20 and then fiber optic strands may be used within the lamps 19,20.

Figure 2:
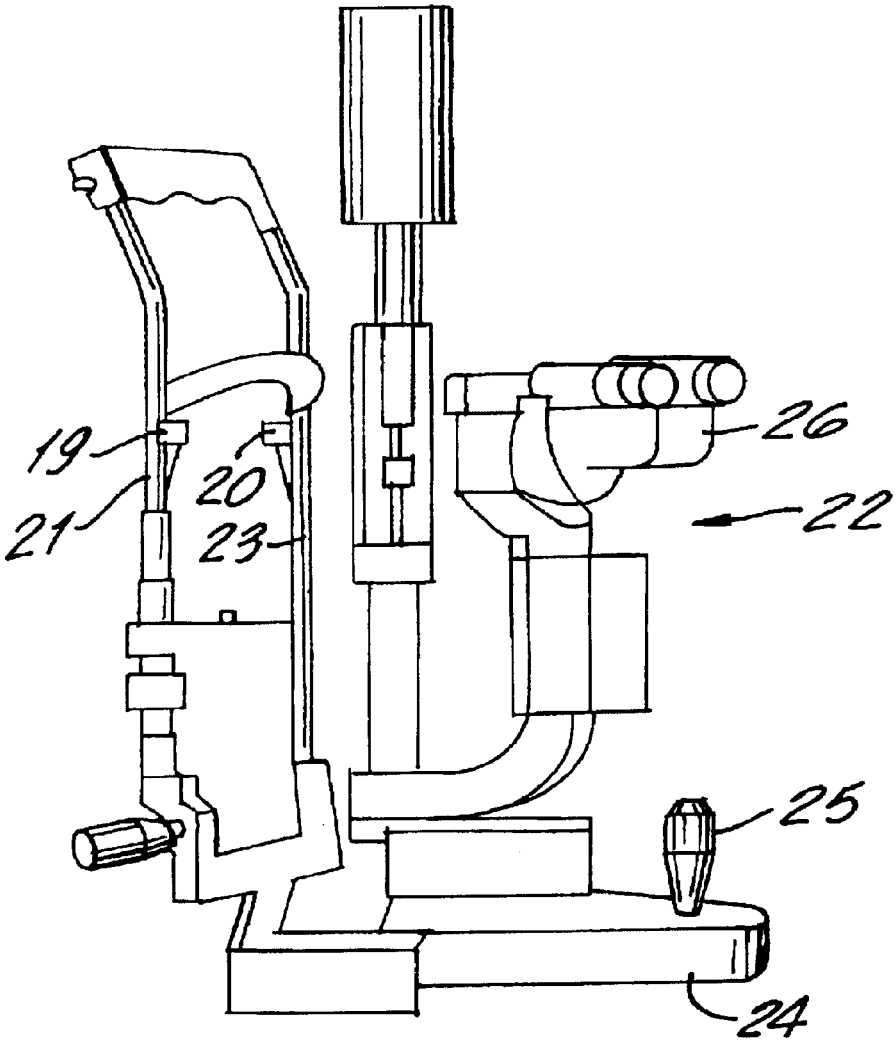
FIG. 2 is a drawing showing two auxiliary lamps mounted on the posts of a slit lamp device.

The lamps 19,20 are the same, except one is mounted on the left frame post 21 of the slit lamp device 22 and the other is mounted on the right frame post 23, see FIG. 2. The structure of the lamps 19,20 is shown in FIGS. 3A–4B.

The lamp casing (housing) 30 is formed from a suitable metal, for example, a steel or aluminum alloy.

The optic fiber strands enter the inner cavity 40 of the casing 30 (see FIG. 4A) and are bent, spread and flattened. Their free ends, which emit the light, are formed, held and glued into an elongated end face 41 (elongated rectangle line, see FIG. 4B), which is preferably 2 cm in height and 0.2 to 0.5 mm wide. The face end 41 is ground and polished.

Figure 3A:
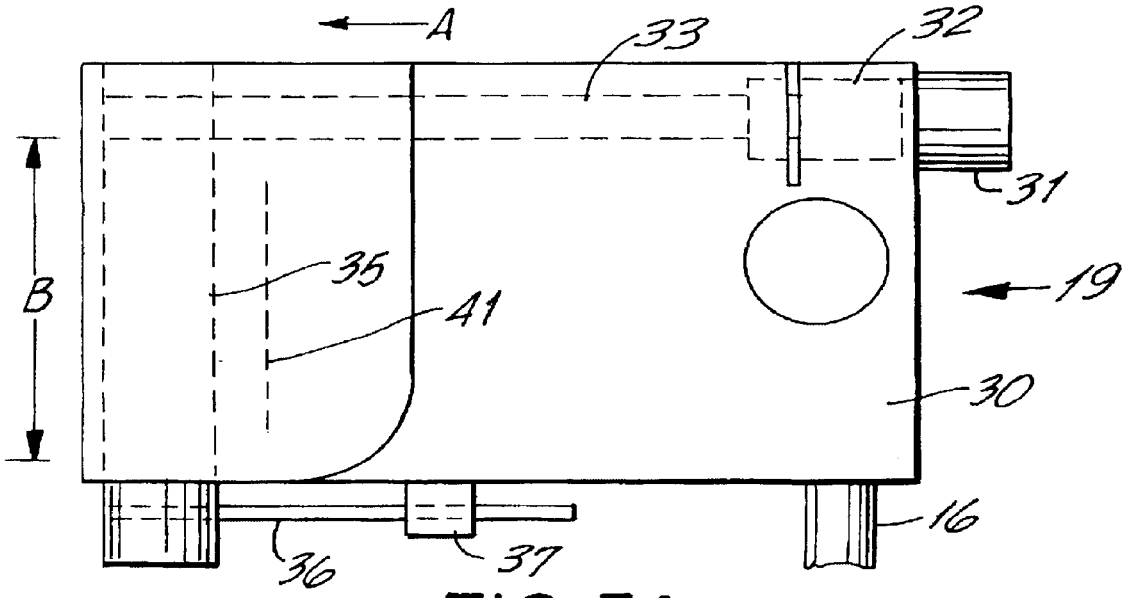
FIG. 3A is a side view of the lamp.

The cylindrical lens 35 is preferably 0.6 cm in diameter, round in cross-sections, and the active portion is preferably 2–3 cm in height (distance B of FIG. 3A). The lens is moved toward, and away from, the end face 41 by rotation of knob 31, in order to focus or diffuse the line of light from the end face 41, see FIG. 3A. The knob 31 is rotatably mounted on casing 30 and is adapted to be turned by the user's fingers. Knob 31 is connected to a nut 32 which is rotatably mounted in casing 30 so that rotation of the knob 31 turns the nut 32. A screw-threaded shaft 33 is partly within nut 32. Rotation of the nut 32 either extends shaft 33 (direction of arrow A) or withdraws shaft 33 (opposite direction to arrow A). The end of shaft 33 extends through a bore at the top of cylindrical lens 35 and is secured to the lens 35. A smooth rod 36, round in cross-section, extends through a bore at the bottom of lens 35 and is secured thereto. The rod 36 acts as a bottom guide rod and is slidingly held in a cavity formed by lips 37 of casing 30.

The lamp may also be used for illumination during skin diagnosis and surgery to provide illumination for digital imaging and to illuminate the operating field. For that purpose the lamp is made larger, i.e., 15 cm high (15 cm height cylindrical lens). For use in dentistry the lamp is made shorter, i.e., 1 cm height (1 cm cylindrical lens) in place of the about 2 cm height lamp used as an auxiliary lamp in a slit lamp device.

Figure 3B:
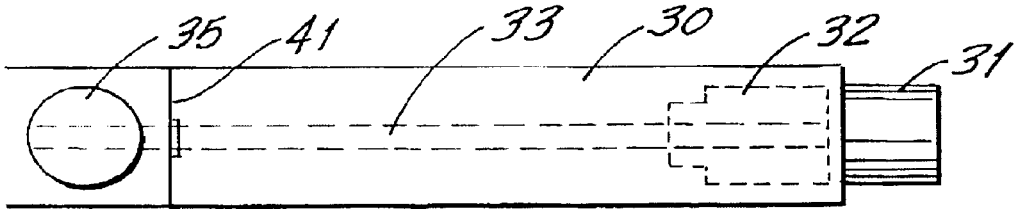
FIG. 3B is a top plan view of the lamp of FIG. 3A.
Figure 3C:
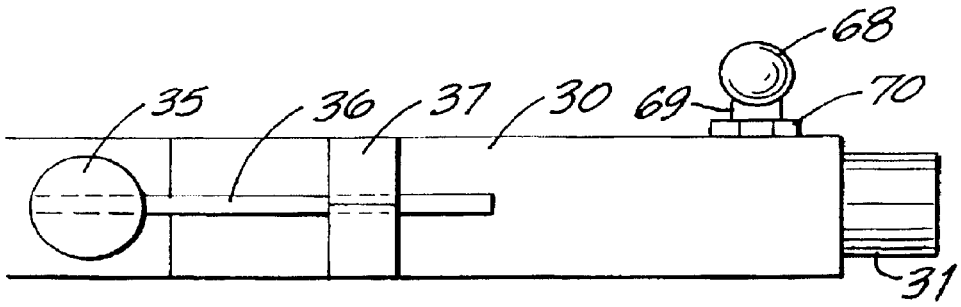
FIG. 3C is a bottom plan view of the lamp of FIG. 3A.

The lens 35 is round in cross-section, see FIGS. 3B and 3C, and is preferably made from optical plastic, such as PMMA or optical glass.

A nut 70 secures a shaft 69 to casing 30, see FIG. 3C. The shaft 69 terminates in a ball 68 which fits into a ball cage 67, see FIG. 5.

Figure 5:
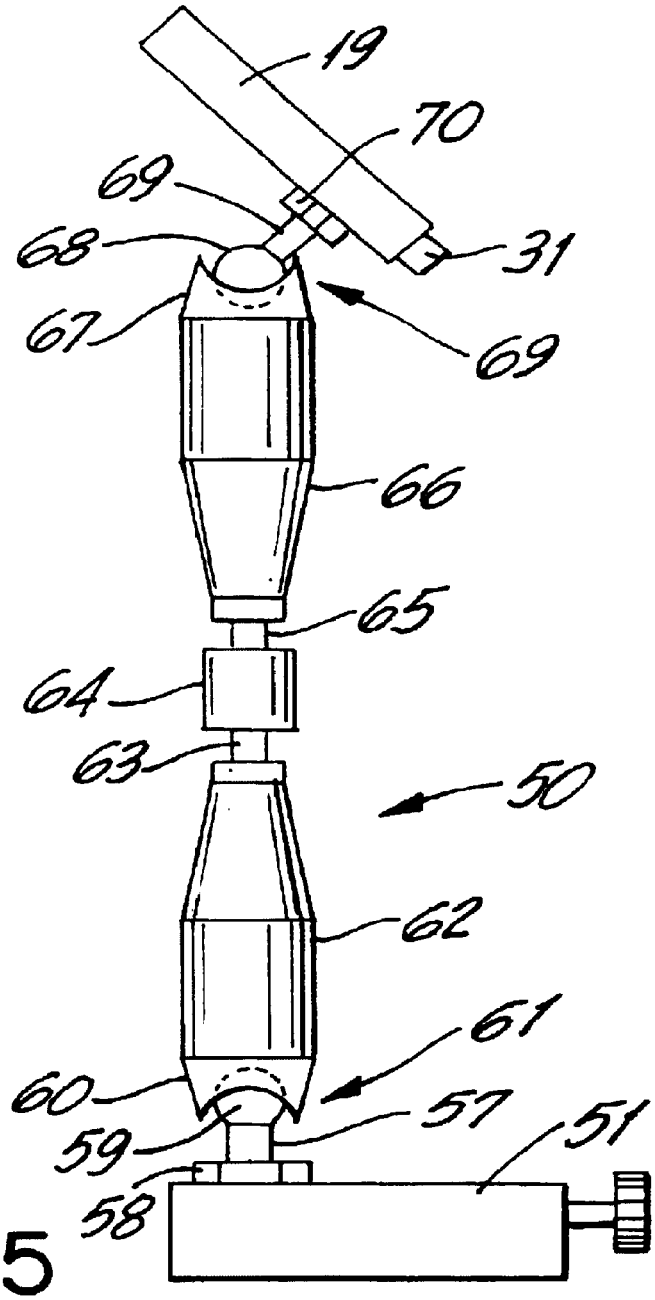
FIG. 5 is a side view of the auxiliary lamp double ball-joint mounting device.
Figure 6:
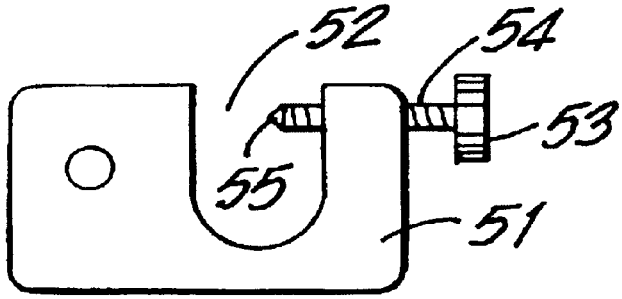
FIG. 6 is a top view of the C-clamp used in the mounting device of FIG. 5.

As shown in FIGS. 5 and 6, the lamp holder 50 is a double ball-joint device which includes a C-clamp 51 which is adapted to be removably fastened to one of the frame posts of the slit lamp. The clamp 51 has a C-shaped opening 52 which fits over the post, a rotatable knob 53 fixed to a screw-threaded shaft 54 which is screwed through a screw-threaded horizontal bore in arm and having a pointed free end 55. A vertically aligned bore in C-clamp 51 receives a shaft 57 which is held fixed in position by nut 58. A ball 59 on the free end of the shaft 57, along with a ball cage 60, forms a ball joint 61. The ball cage 60 is at one end of the tube member 62 and has a shaft 63 at its opposite end. A coupler 64 fixedly holds shaft 63 and shaft 65 of tube member 66. The opposite end of the tube member 66 is a ball cage 67 which holds ball 68 to form a second ball joint 69. The ball 68 is fixed to shaft 69 which is inserted into the lamp 19 and is retained by nut 70.

Figure 7:
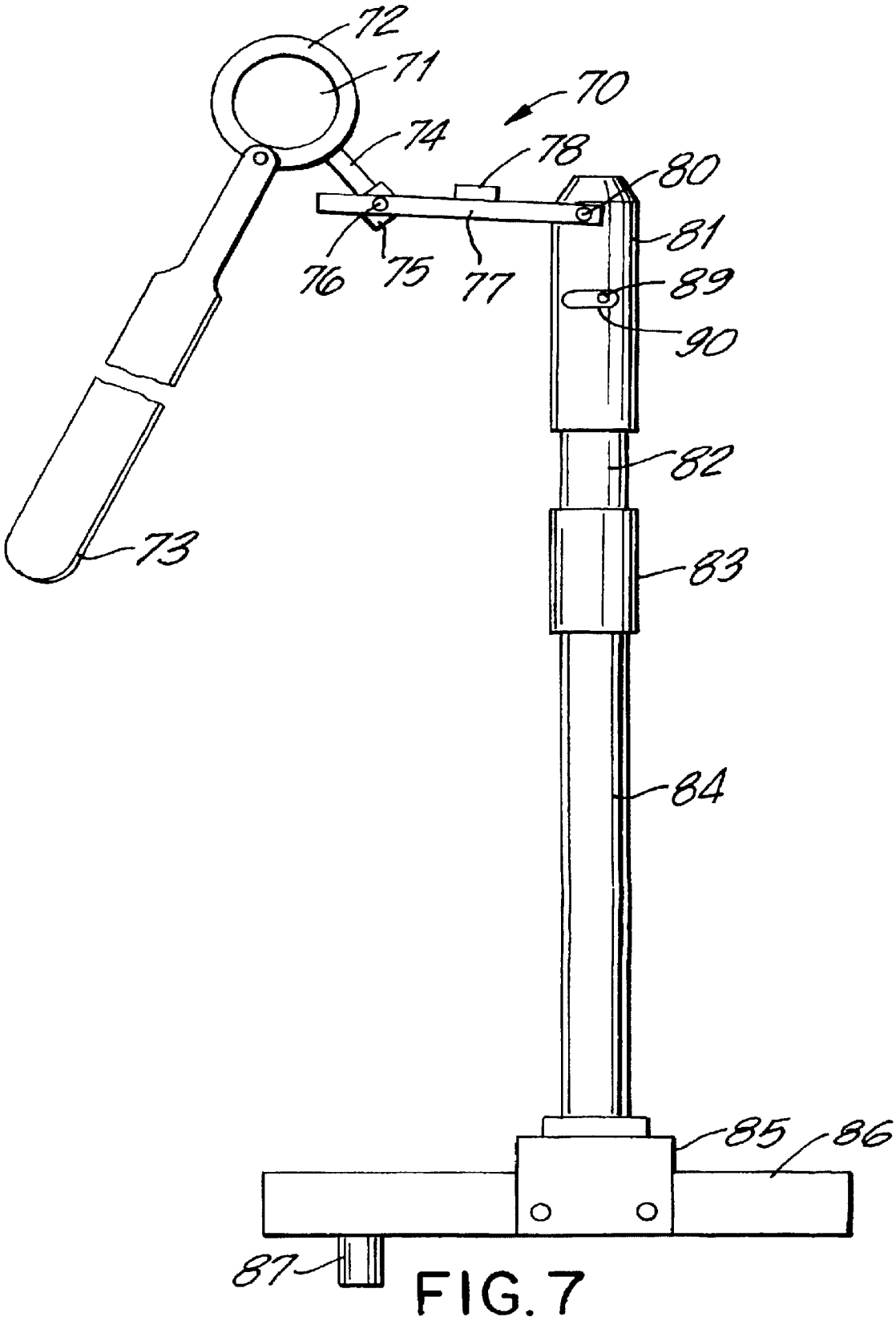
FIG. 7 is a front view of an examination lens and its mounting device.

As shown in FIGS. 7 and 8, a lens holder 70 is adapted to be removably held in the movable base of the slit lamp for visualization of the patient's retina. The ophthalmologist need not hold the lens, which frees his hand, and the lens is held steady, which improves digital photography of the eye. The lens holder is not connected to the chin or headrest supports or the frame posts of the slit lamp device. The lens 71 moves with the stereo microscope, as it is turned relative to the patient's head, so it is maintained in focus, i.e., a set distance from the eyeball after that distance is set by the examiner. As shown in FIG. 2, the user moves the base 24 in the X-Y-Z directions, using a hand-control 25, and the stereo microscope 26 and lens holder (not shown in FIG. 2) move together with movement of the base 24.

The lens 71 is preferably an aspherical double-convex lens in the range of +50 to +160 diopters and is held in ring 72. A handle 73 is fixed to the ring 72 and is used to position the lens 71. The ring 72 has a round plastic shaft portion 74 which is rotatable about its axis within plastic bushing 75. The bushing 75 has two opposite arms 76 which are rotatably mounted in one end of clamp 77. The force on the arms 76 is adjustable by screw 78 of clamp 77. The opposite end of clamp 77 rotatably fits on opposite pins 80 of tube 81. The tube 81 is rotatably mounted on rod 82 and may rotate in a limited arc, i.e., 20 degrees, about the axis of the rod 82 as pin 89 rides within slot 90. The rod 82 is fixed to connector 83 which is fixed at the end of elongated rod 84.

The rod 84 is fixed in bracket 85 which is secured onto plate 86 having a vertically extending bottom shaft 87. The shaft 87 and plate 86 fit on the movable base of the slit lamp so that it moves with the microscope.

The double ball-joint arrangement mounting the auxiliary slit lamp permits it to be moved by the user's fingers and stay in any position. It can be placed so that its beam accurately falls on the eye being examined regardless of the patient's bone structure or size. It permits viewing the eye using a 3D (stereo) microscope to detect eye imperfections.

The fiber optic auxiliary slit lamp may be used simultaneously with the standard slit lamp in conducting the eye examination. Preferably, two fiber optic auxiliary slit lamps (illuminators) are employed to examine a patient's eye. The two lamps are placed in a manner so that both can be used to provide background illumination to the eye being examined. This is accomplished by placing one auxiliary slit lamp at an almost right angle to the eye so the light strikes the eye from the side but is not in the patient's field of vision. The other fiber optic slit illuminator is placed on the other side of the patient's head and may be positioned to cast the line of light over the patient's nose to provide more background illumination to the eye. The standard slit lamp is then used to examine/illuminate specific areas of the eye.

Preferably the slit lamp uses a stereo microscope and a stereo inverter mounted within the microscope.

The preferred stereo inverter is described in U.S. Pat. No. 5,438,456, incorporated by reference. The microscope includes a beam splitter which splits the inverted image, from the aspheric lens, into separated left and right inverted images. The inverter (stereo inverter) comprises a pair of prisms, each prism being a pair of an Abbe Modification of Porro Prisms.

Figure 9:
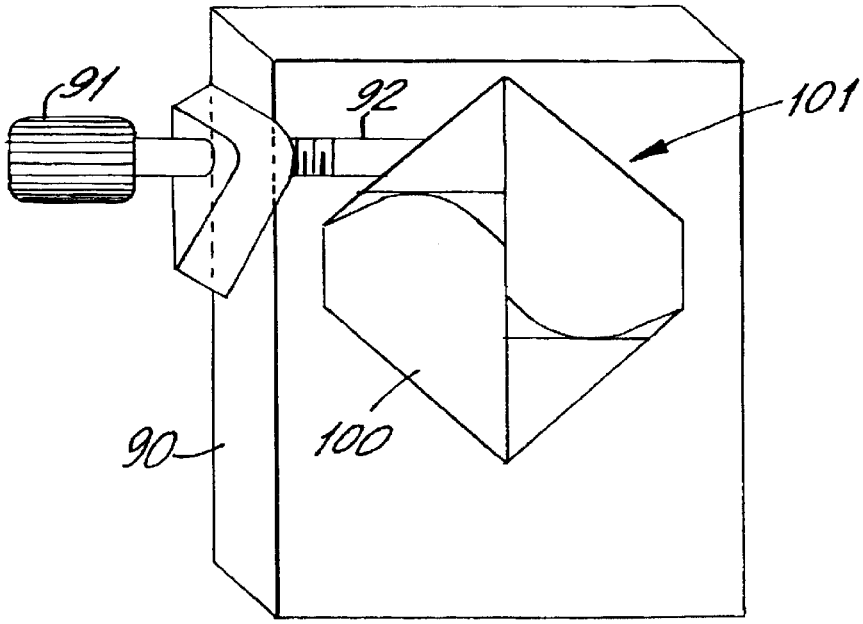
FIG. 9 is a perspective view, illustrating the inverting prism system within its frame.

As shown in FIG. 9, the stereo inverter includes a frame 90 which slides on rails to be inserted in the stereo microscope above the zoom lens ("above" is toward the user) and below the beam amplifier. A knob 91 may be rotated through shaft 92 to adjust the prism assembly 101 within frame 90. The prism assembly consists of two pairs Abbe Modification of Porro Prism. All of the prisms are either left or right—not mixed left and right, and are assembled using optical adhesive.

Figure 8A:
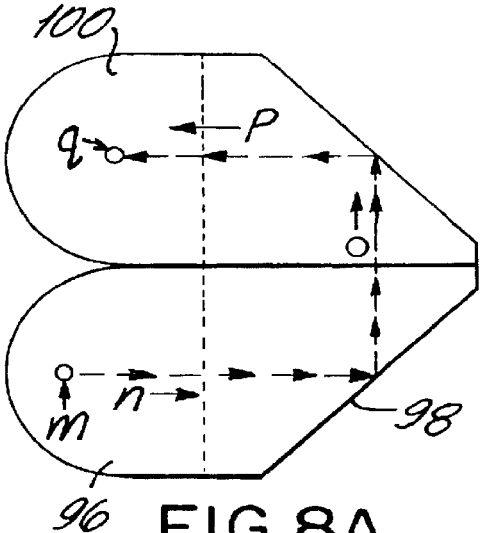
FIGS. 8A and 8B are a side plan view and a top plan view of one pair of prisms.
Figure 8B:
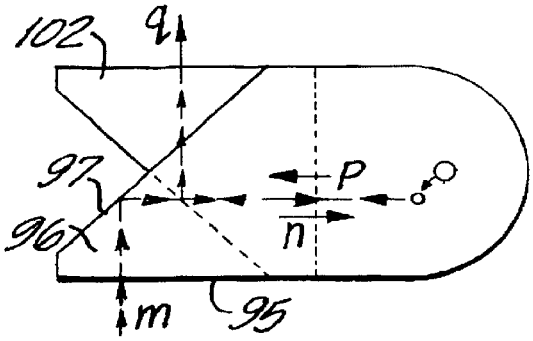

FIGS. 8A and 8B is a side plan view, and top plan view, of one pair of the prisms. The left image is transmitted to the right eyepiece and reinverted. The four prisms of the prism assembly are identical in size, shape and optical properties. The optical image beam m enters from the bottom face 95 of prism 96 and is reflected from a 45-degree angled face 97 to become beam n. In turn, beam n is reflected from 45-degree angled face 98 (see FIG. 8B) to exit as beam o from the side of prism 96. The beam o enters the second prism 100 of the pair and again is internally reflected twice and exits the top of prism 102.

What is claimed is:

1. A lamp system to produce a focusable line of light for examination and photography comprising:

(a) means to generate light including a housing and a bulb within the housing;

(b) a fiber optic cable means to conduct the light from the housing, including a protective sheath and fiber optic strands therein;

(c) a lamp casing and means therein to spread and retain the fiber optic strands to form an elongated terminal end face of the strands;

(d) an elongated lens; and (e) adjustment means to move the lens toward and away from the strands' terminal end face to focus light therefrom into a line of light.

2. A lamp system as in claim 1 and a rotatable disk within the housing of (a) to vary the amount of light transmitted from the bulb to the fiber optic cable.

3. A lamp system as in claim 1 wherein the fiber optic strands comprise at least 1000 glass strands and are randomly arranged within the sheath and terminal end.

4. A lamp system as in claim 1 wherein the lamp system is for eye examination and the lens is in the range of 1.5 cm to 2.5 cm in height.

5. A lamp system as in claim 1 wherein the lamp system is for skin examination and the lens is in the range of 5 cm to 20 cm in height.

6. A lamp system as in claim 1 wherein the lamp system is for dentistry and the lens is in the range of 0.5 to 1.5 cm in height.

7. A lamp system as in claim 1 wherein the lens is a cylindrical lens.

8. A lamp system as in claim 7 wherein the lens in cross-section is uniformly round.

9. A lamp system as in claim 1 wherein the means to move the lens includes, mounted on the lamp casing, a knob adapted to be turned by a user's fingers, a rotatable nut turnable by the knob and connected thereto, and a screw-threaded shaft partly within the nut, the shaft being fixed to the lens.

10. A lamp system as in claim 1 and a double ball-joint connection means to mount the lamp casing on a frame post of a slit lamp device, the connection means including two ball joints for adjustment of the lamp casing relative to the slit lamp device.

11. A lamp system as in claim 1 and a rotatable disc having a plurality of zones, the disc being positioned between the bulb and the fiber optic cable means to vary the amount of light transmitted thereto, each zone having a set of perforations through the disc, with different zones having differently sized perforations.

12. A lamp for eye examination or surgery comprising:

(a) a casing, and within the casing:

(b) a randomly oriented collection of optic fiber strands having free ends;

(c) means to hold the strands' free ends in an elongated end face;

(d) a cylindrical lens to form a line of light; and (e) finger-operable adjustment device to move the lens toward or away from the strands' end face.

13. A lamp as in claim 12 wherein the fiber optic strands comprise at least 1000 glass strands or at least 40 plastic fibers and are randomly arranged.

14. A lamp as in claim 12 wherein the lamp is for eye examination and the lens is in the range of 1.5 cm to 2.5 cm in height.

15. A lamp as in claim 12 wherein the lamp is for skin examination and the lens is in the range of 10 cm to 30 cm in height.

16. A lamp as in claim 12 wherein the lamp is for dentistry and the lens is in the range of 0.5 to 1.5 cm in height.

17. A lamp as in claim 12 wherein the lens in cross-section is uniformly round.

18. A lamp as in claim 12 wherein the adjustment device includes, mounted on the lamp casing, a knob adapted to be turned by a user's fingers, a rotatable nut turnable by the knob and connected thereto, and a screw-threaded shaft partly within the nut, the shaft being fixed to the lens.

19. A lamp system which provides auxiliary illumination and is adapted to be mounted on a slit lamp device, comprising:

(a) a bulb housing and a bulb within the bulb housing;

(b) a fiber optic cable including fiber optic strands and a sheath around the strands;

(c) a fiber optic connector mounted on the housing which is connected to the fiber optic cable;

(d) a lamp casing connected to the fiber optic cable;

(e) fiber optic strands within the lamp casing having free ends with the free ends formed into an elongated end face;

(f) an elongated cylindrical lens of between 1.5 cm and 2.5 cm in height positioned proximate the fiber optic end face to focus light emerging therefrom into a line of light; and (g) an adjustment device connected to the lens and mounted on the lamp housing to move the lens relative to the fiber optic end face.

20. A lamp system as in claim 19 and a rotatable disk within the housing (a) to adjust the amount of light passing from the bulb to the fiber optic cable.

21. A lamp system as in claim 19 wherein the fiber optic strands within the casing comprise at least 1000 glass strands and are randomly arranged.

22. A lamp system as in claim 19 wherein the lens in cross-section is uniformly round.

23. A lamp system as in claim 19 wherein the adjustment device to move the lens includes, mounted on the casing, a knob adapted to be turned by a user's fingers, a rotatable nut turnable by the knob and connected thereto, and a screw-threaded shaft partly within the nut, the shaft being fixed to the lens.

24. A lamp system as in claim 19 and a double ball-joint connection means to mount the lamp casing on the slit lamp device.

25. A lamp system as in claim 19 wherein the slit lamp device has a movable base on which a microscope is mounted, and the slit lamp device includes an aspheric eye examination lens and mounting means to mount the lens on the movable base so that the lens moves with movement of the microscope.

26. A system as in claim 24 wherein the mounting means includes a plurality of bearing means to permit rotational movement.

27. A system as in claim 26 and an image inverter mounted within the microscope.

28. A system as in claim 26 wherein the microscope is a stereo microscope and an image inverter is mounted within the diagnostic microscope.

29. A slit lamp eye examination system comprising:

(a) a slit lamp device including fixed frame posts and a movable base, which base is movable in the X-Y-Z directions under user control;

(b) a microscope mounted on the movable base;

(c) a lens holder mounted on the movable base and including a plurality of joints;

(d) a double convex aspheric lens mounted in the lens holder.

30. A slit lamp system as in claim 29 wherein the joints are ball joints.

31. A slit lamp system as in claim 29 and an image inverter within the microscope to reinvert the image from the aspheric lens.

32. A slit lamp system as in claim 29 and an auxiliary lamp mounted on a frame post and comprising a casing, a fiber optic bundle terminating in an end face within the casing, a cylindrical lens, and an adjustment device mounted on the casing and connected to the cylindrical lens to move the lens toward and away from the end face under user control.

33. A slit lamp system as in claim 29 wherein the microscope is a stereo microscope and a stereo image inverter is mounted within the microscope.

*34. A lamp system to produce a focusable line of light comprising:*

(*a*) *a light source mounted within a housing;*

(*b*) *a fiber optic cable to conduct the light from the housing, wherein the fiber optic cable includes a plurality of fiber optic strands within a protective sheath;*

(*c*) *a lamp casing with ends of the fiber optic strands spread and retained therein to form an elongated terminal end face of the strands;*

(*d*) *an elongated lens; and*

(*e*) *a position adjustment mechanism coupled to the lens to move the lens toward and away from the strands' terminal end face to focus light therefrom into a line of light.*

*35. A lamp system as in claim 34, further comprising a rotatable disk within the housing to vary an amount of light transmitted from the light source to the fiber optic cable.*

*36. A lamp system as in claim 34, wherein the lamp system is for skin diagnosis.*

*37. A lamp system as in claim 36, wherein the lens is in the range of 5 cm to 20 cm in height.*

*38. A lamp system as in claim 34, wherein the lamp system is for eye surgery.*

*39. A lamp system as in claim 38, wherein the lens is in the range of 1.5 cm to 2.5 cm in height.*

*40. A lamp system as in claim 34, wherein the lamp system is for corneal refractive surgery.*

*41. A lamp system as in claim 34, wherein the lamp system provides a preset focus to view one of a patient's eyelids, cornea, iris and an anterior part of a natural lens.*

*42. A lamp system as in claim 34, wherein the position adjustment mechanism includes a knob mounted on the casing for rotation by an operator's fingers and a rotatable nut coupled to the knob for rotation therewith in conjunction with a screw-threaded shaft partly within the nut, the shaft being coupled to the lens.*

*43. A lamp system as in claim 34, further comprising a rotatable disc having a plurality of zones, the disc being positioned between the light source and the fiber optic cable to vary an amount of light transmitted thereto, each zone of the disc including a corresponding set of perforations extending through.*

*44. A lamp comprising:*

(*a*) *a casing;*

(*b*) *a plurality of fiber optic strands having free ends forming an elongated end face within the casing;*

(*c*) *a cylindrical lens for forming a line of light; and*

(*d*) *a finger operable adjustment device to move the lens toward and away from the end face.*

*45. A lamp as in claim 44, wherein the adjustment device includes, mounted on the lamp casing, a knob adapted to be turned by a user's fingers, a rotatable nut turnable by the knob and connected thereto and a screw-threaded shaft partly within the nut, the shaft being fixed to the lens.*

*46. A lamp system as in claim 44, wherein the lamp system is for skin diagnosis.*

*47. A lamp system as in claim 46, wherein the lens is in the range of 5 cm to 20 cm in height.*

*48. A lamp system as in claim 44, wherein the lamp system is for eye surgery.*

*49. A lamp system as in claim 48, wherein the lens is in the range of 1.5 cm to 2.5 cm in height.*

*50. A lamp system as in claim 44, wherein the lamp system is for dentistry.*

*51. A lamp system as in claim 50, wherein the lens is in the range of 0.5 cm to 1.5 cm in height.*

*52. A slit lamp comprising:*

(*a*) *a moveable base and a plurality of fixed frame posts, wherein the base is moveable in each of X, Y and Z directions under user control;*

(*b*) *a microscope mounted on the moveable base;*

(*c*) *a lens holder mounted on the movable base and including a plurality of joints; and*

(*d*) *a double convex aspheric lens mounted in the lens holder.*

*53. A slit lamp system as in claim 52, further comprising an image inverter within the microscope to reinvert an image from the aspherical lens.*

*54. A slit lamp system as in claim 52, further comprising an auxiliary lamp mounted on a first one of the frame posts, the auxiliary lamp comprising a casing, a fiber optic bundle terminating in an end face within the casing, a cylindrical lens and an adjustment device to move the cylindrical lens toward and away from the end face under user control.*

* * * * *